United States Patent
Grashow et al.

(10) Patent No.: US 11,642,483 B2
(45) Date of Patent: May 9, 2023

(54) PATIENT INTERFACE STABILIZATION DEVICE

(71) Applicant: KONINKLIJKE PHILIPS N.V., Eindhoven (NL)

(72) Inventors: Jonathan Sayer Grashow, Pittsburgh, PA (US); Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 611 days.

(21) Appl. No.: 16/444,834

(22) Filed: Jun. 18, 2019

(65) Prior Publication Data
US 2019/0388639 A1    Dec. 26, 2019

Related U.S. Application Data

(60) Provisional application No. 62/688,605, filed on Jun. 22, 2018.

(51) Int. Cl.
*A61M 16/00* (2006.01)
*A61M 16/06* (2006.01)

(52) U.S. Cl.
CPC .... *A61M 16/0683* (2013.01); *A61M 16/0622* (2014.02); *A61M 16/0666* (2013.01)

(58) Field of Classification Search
CPC .......... A61M 16/0683; A61M 16/0622; A61M 16/0666; A61M 16/0605; A61M 16/06;
(Continued)

(56) References Cited

U.S. PATENT DOCUMENTS 9,480,809 B2 * 11/2016 Guney ................. A61M 16/06
2004/0226566 A1  11/2004 Gunaratnam et al.
(Continued)

FOREIGN PATENT DOCUMENTS

WO    2005018523 A2    3/2005
WO    2008011682 A1    1/2008
(Continued)

OTHER PUBLICATIONS efunda.com, Thermoplastic Elastomers material properties (ASM Metals Reference Book, 3rd ed., ASM International (Materials Park, OH). (Year: 1993).*
(Continued)

*Primary Examiner* — Philip R Wiest
*Assistant Examiner* — Sarah B Lederer
(74) *Attorney, Agent, or Firm* — Michael W. Haas

(57) ABSTRACT

A headgear assembly includes a first arm member and a second arm member each having a first end and a second, opposing end. The first end of the first arm member has a structure sized and configured to engage a first rotation-resistant coupling of a frame in a manner which prohibits rotation of the first arm member with respect to the frame in a first plane in which the first arm member is located. The first end of the second arm member has a structure sized and configured to engage a second rotation-resistant coupling of the frame in a manner which prohibits rotation of the second arm member with respect to the frame in a second plane in which the second arm member is located. The assembly further includes a strap member coupled to the first and second arm members.

11 Claims, 6 Drawing Sheets

(58) Field of Classification Search
CPC ............ A61M 16/00; A61B 2090/502; A62M 16/0683–0694
See application file for complete search history.

(56) References Cited

U.S. PATENT DOCUMENTS

| | | |
|---|---|---|
| 2006/0081250 A1 | 4/2006 | Bordewick |
| 2008/0060649 A1 | 3/2008 | Veliss et al. |
| 2008/0190432 A1* | 8/2008 | Blochlinger ...... A61M 16/0616 128/207.18 |
| 2009/0038619 A1* | 2/2009 | Ho .................... A61M 16/0605 128/206.24 |
| 2011/0220113 A1 | 9/2011 | Newman |
| 2015/0328423 A1* | 11/2015 | Siew ................ A61M 16/0616 128/205.25 |
| 2017/0281894 A1* | 10/2017 | Walls ................ A61M 16/0683 |
| 2019/0224438 A1 | 7/2019 | Grashow |

FOREIGN PATENT DOCUMENTS

| | | | |
|---|---|---|---|
| WO | 2012167327 A1 | 12/2012 | |
| WO | 2015079396 A1 | 6/2015 | |
| WO | WO-2017124155 A1 * | 7/2017 | ............ A61M 16/06 |

OTHER PUBLICATIONS

Engineering ToolBox, (2003). Young's Modulus, Tensile Strength and Yield Strength Values for some Materials, [online] Available at: https://www.engineeringtoolbox.com/young-modulus-d_417.html [Accessed Day Mo. Year], (Year: 2003).*

* cited by examiner

PATIENT INTERFACE STABILIZATION DEVICE

CROSS-REFERENCE TO RELATED APPLICATIONS

This patent application claims the priority benefit under 35 U.S.C. § 119(e) of U.S. Provisional Application No. 62/688,605, filed on Jun. 22, 2018, the contents of which are herein incorporated by reference.

BACKGROUND OF THE INVENTION

1. Field of the Invention

The present invention pertains to airway pressure support systems for use in delivering a flow of a humidified gas to the airway of a patient. The present invention also relates to patient interface devices for airway pressure support systems, and headgear assemblies for the same.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

In order to secure the patient interface device to the head of the patient, many known patient interface devices include headgear assemblies. Some headgear assemblies include a single strap member which is coupled to opposing sides of a frame member of the patient interface device. The strap member typically extends around the back of the head of the patient in order to ensure that the cushion is pulled onto the patient at or about the patient's airway. One known problem with existing headgear assemblies is that the strap member often does not stay maintained on the head of the patient. Specifically, it is common that during use, such as while the patient is sleeping, the strap member may slide up the back of the head of the patient. In this situation, the forces that previously maintained engagement between the cushion and the patient would be significantly reduced, thus compromising the integrity of the pressure support therapy.

SUMMARY OF THE INVENTION

Accordingly, it is an object of the present invention to provide an improved airway pressure support system, and patient interface device and headgear assembly for the same.

In accordance with one aspect of the disclosed concept, a headgear assembly is provided for use in a patient interface having a frame member and a cushion for delivering a flow of a breathing gas to the airway of a patient, the frame member having a first rotation-resistant coupling and a second rotation-resistant coupling defined therein. The headgear assembly includes a first arm member and a second arm member, each arm member having a first end and a second end located opposite the first end, the first end of the first arm member having a structure sized and configured to selectively engage the first rotation-resistant coupling in a manner which prohibits rotation of the first arm member with respect to the frame member in a first plane in which the first arm member is located, and the first end of the second arm member having a structure sized and configured to selectively engage the second rotation-resistant coupling in a manner which prohibits rotation of the second arm member with respect to the frame member in a second plane in which the second arm member is located; and a strap member coupled to the first arm member and the second arm member, and extending between the second end of the first arm member and the second end of the second arm member.

In accordance with another aspect of the disclosed concept, a patient interface device is provided for an airway pressure support system. The airway pressure support system has a hose and a gas flow generator configured to generate a flow of breathing gas. The patient interface device includes a cushion configured to receive the flow of breathing gas and deliver the flow of breathing gas to an airway of a patient; a frame member coupled to the cushion; a coupling member coupled to the frame member and structured to be coupled to the hose in order to communicate the flow of breathing gas from the gas flow generator to the frame member, the coupling member being fluidly coupled to and located opposite and distal the cushion; and a headgear assembly having a first arm member and a second arm member each including a first end and a second end located opposite the first end, each respective first end being directly coupled to the frame member, and a strap member coupled to the first arm member and the second arm member and extending therebetween. Each respective first end is located closer to the coupling member than each respective second end and the strap member.

In accordance with another aspect of the disclosed concept, an airway pressure support system includes a hose, a gas flow generator configured to generate a flow of breathing gas, and the aforementioned patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
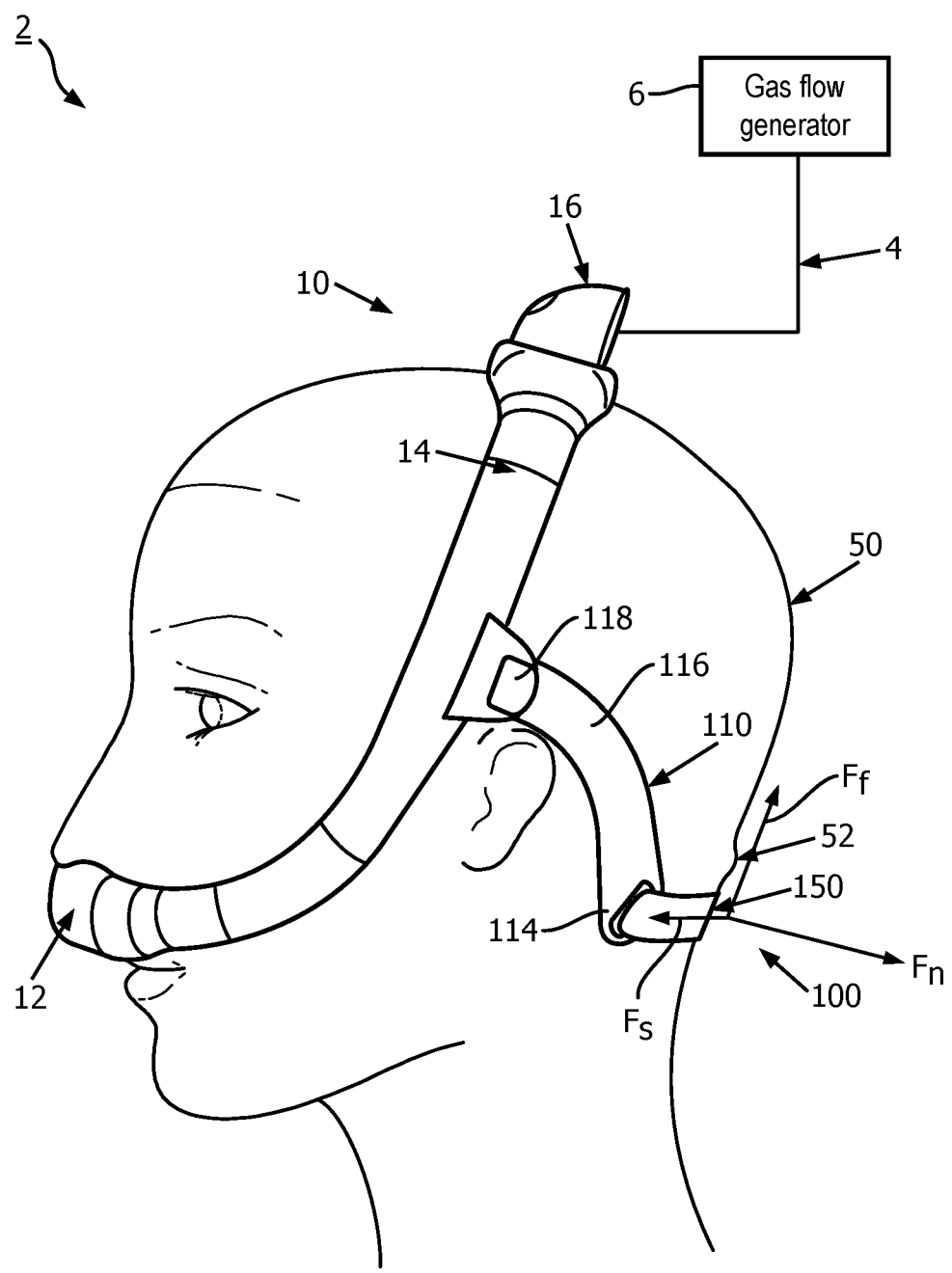
FIG. 1 is a partially simplified side elevation view of an airway pressure support system and patient interface device for the same, shown employed on a patient, in accordance with one non-limiting embodiment of the disclosed concept.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are joined or coupled together directly and are in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a side elevation view of an airway pressure support system 2 and patient interface device 10 for the same, in accordance with one non-limiting embodiment of the disclosed concept. Pressure support system 2 further includes a hose 4 (shown in simplified form) and a gas flow generator 6 (shown in simplified form). In operation, gas flow generator 6 is configured to generate a flow of breathing gas, which, via hose 4, is passed into patient interface device 10.

Patient interface device 10 includes a cushion 12, a frame member 14 coupled to cushion 12, and a coupling member (e.g., without limitation, elbow 16) coupled to frame member 14. It will be appreciated that elbow 16 is coupled to hose 4 in order to communicate the flow of breathing gas from gas flow generator 6 to frame member 14. As frame member 14 preferably defines a fluid pathway configured to be disposed on opposing sides of the head of patient 50, it follows that frame member 14 fluidly couples elbow 16 to cushion 12. Stated differently, elbow 16 is fluidly coupled to and located opposite and distal cushion 12. In this manner, cushion 12 is able to deliver the flow of breathing gas to the airway of patient 50.

Figure 2:
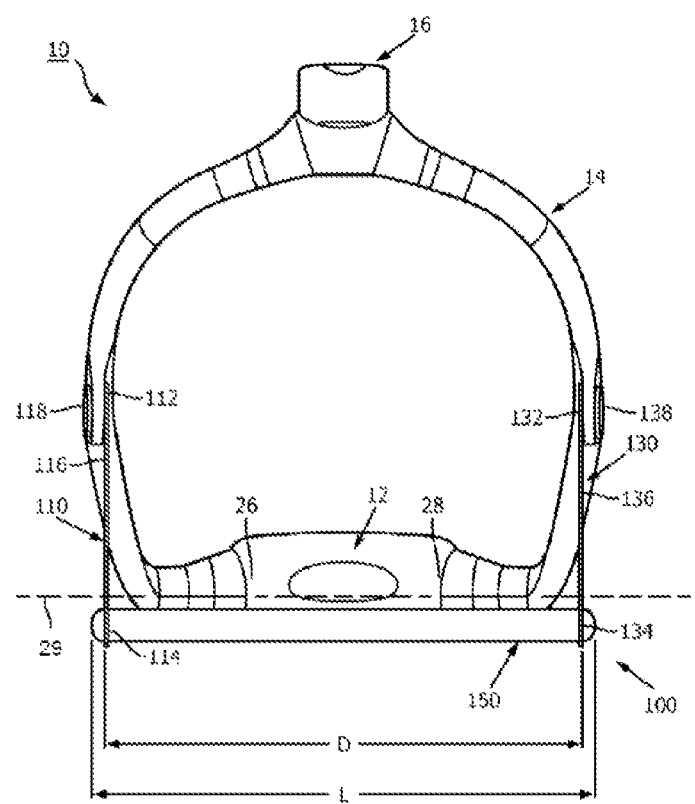
FIG. 2 is a rear view of the patient interface device of FIG. 1.

In accordance with the disclosed concept, patient interface device 10 further includes a novel headgear assembly 100 configured to minimize and/or eliminate the possibility that a strap will slip off of the head of patient 50 while therapy is being delivered. Referring to FIG. 2, headgear assembly 100 includes a first arm member 110, a second arm member 130 located opposite first arm member 110, and a strap member 150. Each arm member 110, 130 includes a first end 112, 132, a second end 114, 134 located opposite first end 112, 132, and a body portion 116, 136 extending in a curved manner between first end 112, 132 and second 114, 134.

Specifically, second end 114 of first arm member 110 is spaced first and second distances from cushion 12 and elbow 16, respectively. Second end 134 of second arm member 130 is spaced third and fourth distances from cushion 12 and elbow 16, respectively. The first and third distances are the same, and the second and fourth distances are the same. In one example embodiment, as shown in FIG. 1, arm members 110 (i.e., and second arm member 130, not shown in FIG. 1, but see FIGS. 2-4) are concave facing the corresponding ears of patient 50 such that second ends 114, 134 are configured to be located at or about the same elevation as the base of the ears and behind the ears of patient 50. In this manner, each of first ends 112, 132 are preferably located closer to elbow 16 than second ends 114, 134 and strap member 150, the advantages of which will become more apparent below. Continuing to refer to FIG. 2, cushion 12 has a first end portion 26 and a second end portion 28 located opposite and distal first end portion 26. As shown, first and second end portions 26,28, and first and second ends 114, 134 are substantially located in a plane 29. Furthermore, elbow 16 is located opposite and distal plane 29.

Figure 3:
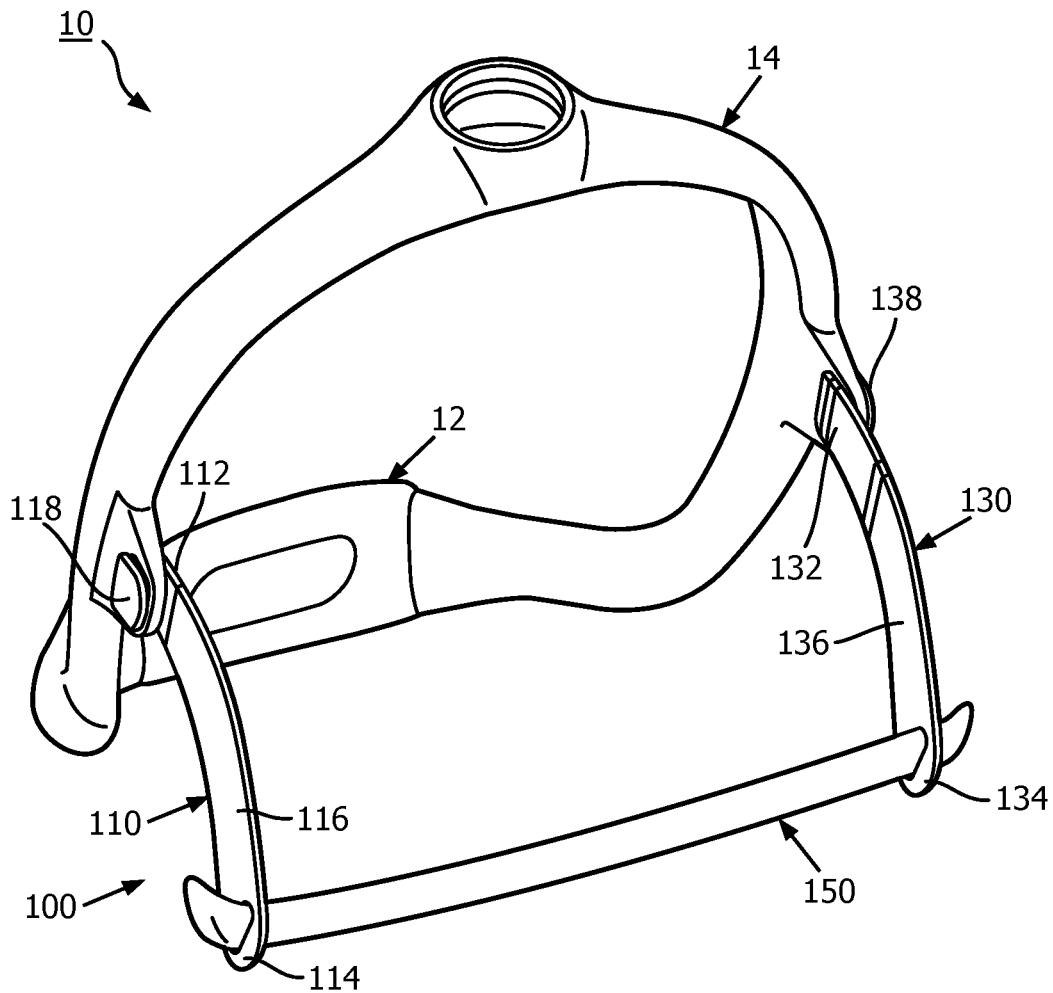
FIG. 3 is a rear isometric view of the patient interface device of FIG. 2, shown without a coupling member.
Figure 4:
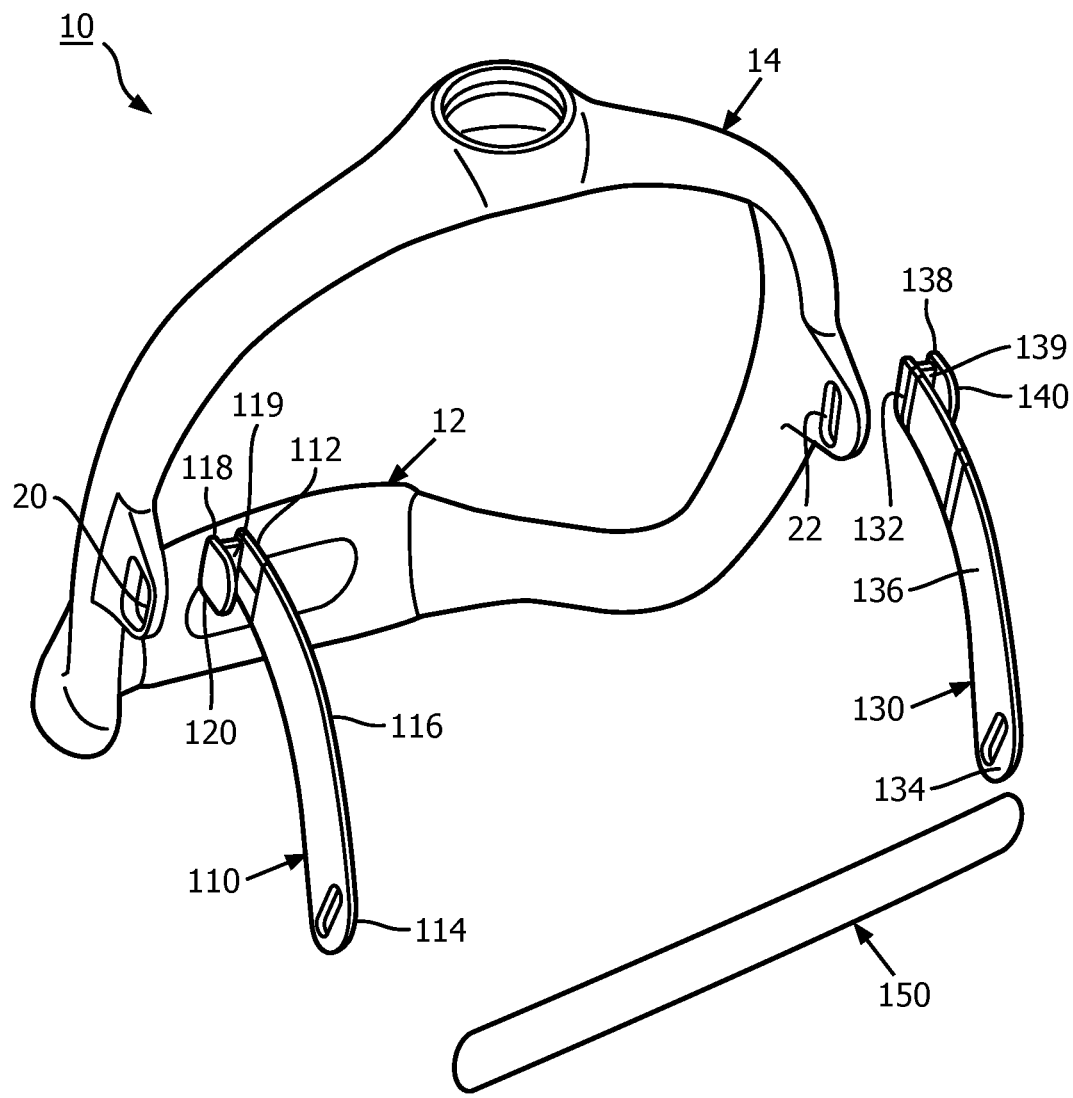
FIG. 4 is a rear isometric view of the patient interface device of FIG. 3, shown with the first and second arm members, and the strap member, exploded.

First ends 112,132 of arm members 110,130 are preferably directly coupled to frame member 14. FIGS. 1-4 show one example embodiment of the disclosed concept wherein arm members 110, 130 are removably coupled to frame member 14. For example, as shown in FIGS. 3 and 4, frame member 14 has first and second rotation-resistant couplings (e.g., without limitation, elongated slots 20, 22). It will be appreciated that first end 112 has a structure (e.g., without limitation, a structure including a hook-shaped portion 118) that is sized and configured to selectively engage first elongated slot 20 in a manner which prohibits rotation of first arm member 110 with respect to frame member 14 in a first plane in which first arm member 110 is located. Similarly, it will be appreciated that first end 132 of second arm member 130 has a structure (e.g., without limitation, a structure including a hook-shaped portion 138) that is sized and configured to selectively engage second elongated slot 22 in a manner which prohibits rotation of second arm member 130 with respect to frame member 14 in a second plane in which second arm member 130 is located.

As a result of the aforementioned coupling between arm members 110, 130 and frame member 14, when patient interface device 10 is donned by patient 50, second ends 114, 134 are structured to be maintained behind and at the same elevation as the base of the ears of patient 50. Referring again to FIG. 2, strap member 150 is coupled, preferably adjustably coupled to second ends 114, 134 of arm members 110, 130 and extends therebetween. It will also be appreciated that suitable alternative strap members (not shown) may be non-adjustably coupled to arm members 110, 130, such as, without limitation, via a connection wherein the strap member is sewn onto second ends 114, 134 of arm members 110, 130.

Furthermore, arm members 110,130 are preferably made of a material (e.g., without limitation, a thermoplastic material) that is more rigid and different than strap member 150. Non-limiting examples of materials from which strap member 150 may be made include fabric, fabric/foam laminates, elastomers such as silicone and thermoplastic elastomers, elastic, and/or fabric-covered elastomers. In one example embodiment, arm members 110, 130 each have a Young's modulus of greater than 0.1 Gigapascals, and a durometer of between 80 Shore A to 100 Shore D. Accordingly, when patient interface device 10 is donned by patient 50, the relatively rigid arm members 110, 130 also function to maintain strap member 150 in the position depicted in FIGS. 1-3. In this manner, it will be appreciated that potential upward movements of strap member 150 (from the perspective of FIG. 1) will immediately be resisted by arm members 110, 130, specifically by the connection between arm members 110, 130 and frame member 14. Thus, headgear assembly 100 substantially minimizes and/or eliminates the likelihood that patient interface device 10 will slide off of the head of patient 50 when pressure support therapy is being delivered.

Additionally, as shown in FIG. 1, such arrangement of arm members 110,130 positions strap member below the occipital bone 52 of patient 50 (as viewed when the patient's head is in an upright position such as shown in FIG. 1) when patient interface device 10 is donned by patient 50, thereby providing another mechanism to minimize and/or eliminate the likelihood that patient interface device 10 will slide off of the head of patient 50. Specifically, strap member 150 is preferably located at the base of the head of patient 50 such that strap member 150 would have to flex a relatively large distance to pass by occipital bone 52, which protrudes outwardly a significant distance from the head of patient 50. Additionally, as shown in FIG. 2, second end 114 of first arm member 110 is spaced a distance D from second end 134 of second arm member 130, and strap member 150 has a length L. While strap member 150 may flex a bit when patient interface device 10 is donned by patient 50, it will be appreciated that length L may preferably generally be the same as distance D. See also, for example, FIG. 1, wherein it can be seen that strap member 150 is not structured to bow a significant amount, as compared to an arrangement wherein a different strap member might extend around the head of the patient above the occipital bone. In these arrangements the strap member is relatively long, and as a result are prone to slippage.

Continuing to refer to FIG. 1, it will be appreciated that because of the position of second ends 114, 134 with respect to the head of patient 50, strap member 150 is configured to exert a force $F_S$ on the head of patient 50. The resisting force generally includes a normal force component $F_N$ perpendicular to the head of patient 50, and a friction force component $F_F$ parallel to the surface of the head of patient 50. It will be appreciated with reference to FIG. 1 that force $F_S$ is perpendicular to or below (e.g., closer to the neck of patient 50) normal force component $F_N$. As a result, patient interface device 10 generally preferably does not rely on frictional forces between strap member 150 and patient 50 to be maintained on the head of patient 50. Specifically, it can be appreciated that headgear assembly 100 is aligned so as to pull strap member 50 further down (with respect to the orientation of FIG. 1) toward the neck of patient 50 rather than up toward the crown.

As stated above, first and second arm members 110, 130 preferably have hook-shaped portions 118, 138 sized to engage slots 20,22 of frame member 14. Hook-shaped portions 118, 138 each include respective intermediate portions 119,139 extending from and being located generally perpendicular to body portions 116, 136, and retaining portions 120, 140 extending from and being located perpendicular to intermediate portions 119, 139. Hook-shaped portions 118, 138 provide a mechanism by which first ends 112, 132 can be removably coupled to frame member 14, and provide a mechanism by which undesired rotation of arm members 110, 130 can be resisted. Specifically, referring to FIG. 1, if arm members 110 (e.g., and 130, not shown in FIG. 1) were to begin to rotate in the counterclockwise direction, the connection between hook-shaped portions 118, 138 and frame member 14 would advantageously resist such rotation. In one example embodiment, intermediate portions 119, 139 are sized to fill slots 20,22 and/or engage with the edges of frame member 14 defining said slots 20, 22.

Figure 5:
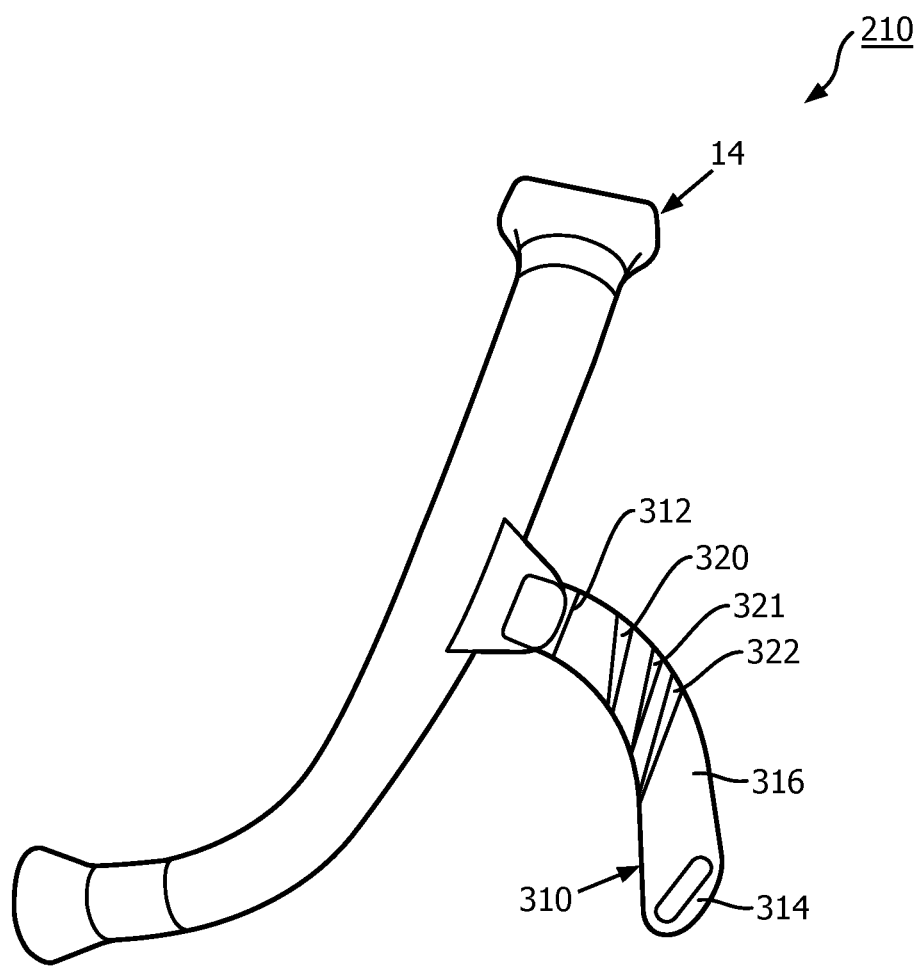
FIG. 5 is a side elevation view of a portion of another patient interface device, in accordance with another non-limiting embodiment of the disclosed concept.

FIG. 5 shows a right side elevation view of a portion of another patient interface device 210, in accordance with another non-limiting embodiment of the disclosed concept. Patient interface device 210 has all of the same advantages as patient interface device 10, and like reference numbers represent like elements. Additionally, as shown in FIG. 5, first arm member 310 has a number of living hinges (three example living hinges 320, 321, 322) located in body portion 316 between first and second ends 312,314. Hinges 320, 321, 322 may be thinned or weakened regions of body portion 316, and advantageously allow first arm member 310 to bend around the head of the patient while still resisting bending moments between frame member 14 a strap member (not shown in FIG. 5, but see strap member 150 of patient interface device 10, discussed above). While the disclosed concept has been described herein in association with first arm member 310 having hinges 320, 321, 322 to allow for the advantageous bending around the head of the patient, it will be appreciated that a suitable alternative arm member (not shown) may have slots in its body portion in addition to and/or instead of hinges, without departing from the scope of the disclosed concept. It will also be appreciated that a second arm member (not shown) opposing first arm member 310 may also have hinges and/or slots, or any suitable arrangement/structure which provides for lessor stiffness, in a similar manner as first arm member 310, without departing from the scope of the disclosed concept.

Figure 6:
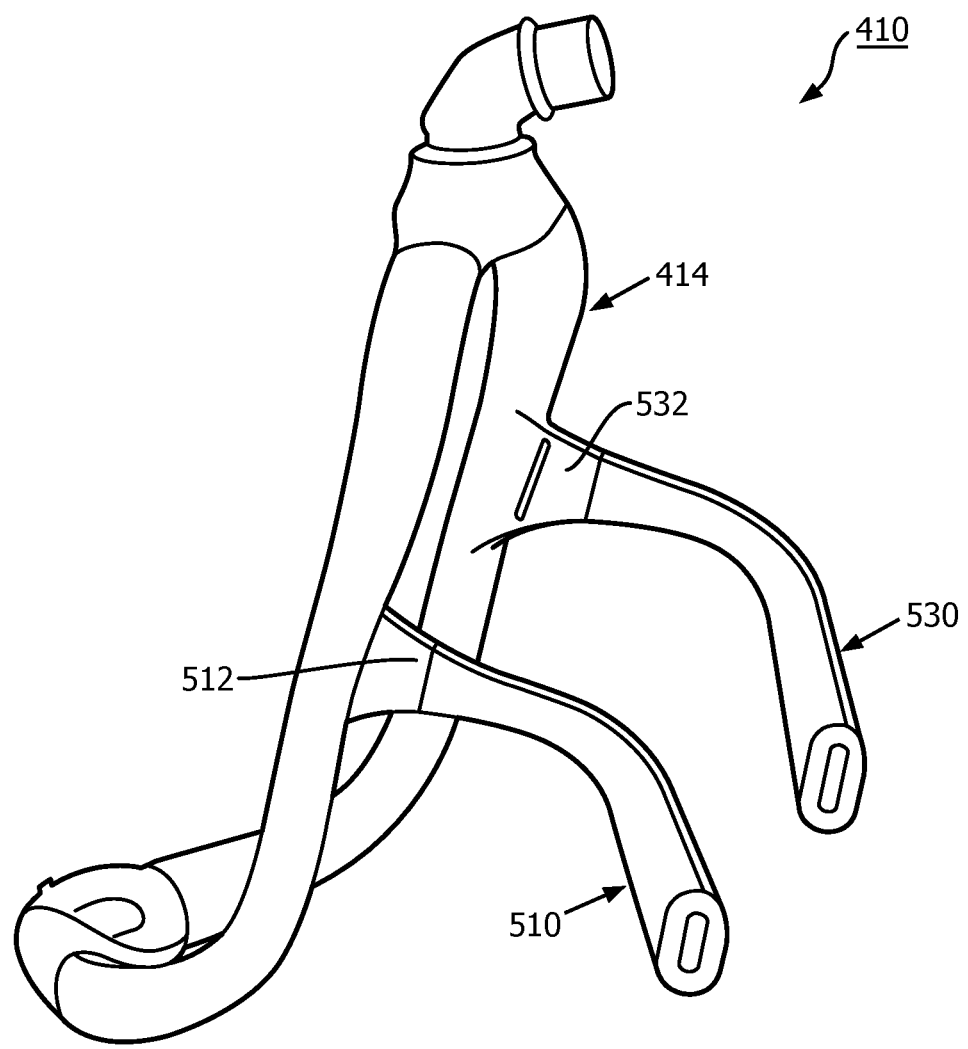
FIG. 6 is a side isometric view of another patient interface device, in accordance with another non-limiting embodiment of the disclosed concept.

FIG. 6 shows a side isometric view of a portion of another patient interface device 410, in accordance with another non-limiting embodiment of the disclosed concept. Patient interface device 410 has all of the same advantages as patient interface devices 10, 210, and like reference numbers represent like elements. Additionally, patient interface device 410 is structured differently from patient interface devices 10,210. Specifically, first ends 512, 532 of arm members 510, 530 are configured to be fixedly coupled to frame member 414. First ends 512, 532 may be coupled to frame member 414 by an overmolding procedure, a co-molding procedure, and/or via adhesives.

Accordingly, it will be appreciated that in each of patient interface devices 10, 210, 410, when assembled, first arm members 110, 310, 510 and second arm members 130, 530 are each generally fixed with respect to corresponding frame members 14, 414. As a result, and as stated above, the likelihood of any undesirable rotation of arm members 110, 130, 310, 510, 530 with respect to corresponding frame members 14,514 is significantly minimized.

It will be appreciated that the disclosed concept provides for an improved (e.g., without limitation, better protected against slippage (e.g., unintended sliding of strap members)) airway pressure support system 2, and patient interface device 10,210,410 and headgear assembly 100 for the same, in which a strap member 150 is advantageously maintained at a base of the head of a patient 50.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A headgear assembly for use in a patient interface device having a frame member and a cushion coupled thereto for delivering a flow of a breathing gas to the airway of a patient, the frame member having: a top portion structured to be positioned centrally at a top portion of the head of a patient when the frame member is positioned on the head of the patient, a first portion sized and configured to extend from the top portion toward the cushion along a first side of the head of the patient when the frame member is positioned on the head of the patient, the first portion including a first rotation-resistant coupling positioned along the first portion so as to be disposed adjacent an ear of the patient when the frame member is disposed on the head of the patient, and a second portion sized and configured to extend from the top portion toward the cushion along a second side of the head of the patient opposite the first side when the frame member is positioned on the head of the patient, the second portion including a second rotation-resistant coupling positioned along the second portion so as to be disposed adjacent another ear of the patient when the frame member is disposed on the head of the patient, the headgear assembly comprising:

a first arm member and a second arm member, each arm member comprising a first end and a second end disposed opposite the first end, the first end of the first arm member having a structure sized and configured to selectively engage the first rotation-resistant coupling in a manner which prohibits rotation of the first arm member with respect to the frame member in a first plane in which the first arm member is disposed, and the first end of the second arm member having a structure sized and configured to selectively engage the second rotation-resistant coupling in a manner which prohibits rotation of the second arm member with respect to the frame member in a second plane in which the second arm member is disposed; and a strap member coupled to the first arm member and the second arm member, and extending between each of the second end of the first arm member and the second end of the second arm member, wherein the first arm member comprises a body portion sized and configured to extend behind the ear of the patient when the headgear assembly is disposed on the head of the patient, and wherein the second arm member comprises a body portion sized and configured to extend behind the other ear of the patient when the headgear assembly is disposed on the head of the patient.

2. The headgear assembly of claim 1, wherein each of the first rotation-resistant coupling and the second rotation-resistant coupling is an elongated slot; and wherein the structure of the first end of each arm member comprises a hook-shaped portion.

3. The headgear assembly of claim 1, wherein the strap member is adjustably coupled to at least one of the first arm member and the second arm member.

4. The headgear assembly of claim 1, wherein the body portion of each of the first arm member and the second arm member extends in a curved manner between the first end and the second end.

5. The headgear assembly according to claim 1, wherein each of the first arm member and the second arm member has a Young's modulus of greater than 0.1 Gigapascals.

6. The headgear assembly according to claim 1, wherein each of the first arm member and the second arm member comprises a body portion, and wherein the body portion of at least one of the arm member and the second arm member comprises at least one living hinge.

7. The headgear assembly of claim 4, wherein when positioned on the head of the patient the body portion of the first arm member is concave facing the ear of the patient and the body portion of the second arm member is concave facing the other ear of the patient.

8. A patient interface device for an airway pressure support system for use in delivering a flow of a breathing gas to the airway of a patient, the airway pressure support system comprising a hose and a gas flow generator configured to generate a flow of breathing gas, the patient interface device comprising:

a cushion structured to receive the flow of breathing gas and deliver the flow of breathing gas to the airway of the patient;

a frame member coupled to the cushion, the frame member comprising:

a top portion structured to be positioned centrally at a top portion of the head of the patient when the frame member is positioned on the head of the patient;

a first portion sized and configured to extend from the top portion toward the cushion along a first side of the head of the patient when the patient interface device is positioned on the head of the patient, the first portion including a first rotation-resistant coupling positioned along the first portion so as to be disposed adjacent an ear of the patient when the patient interface device is disposed on the head of the patient, and a second portion sized and configured to extend from the top portion toward the cushion along a second side of the head of the patient opposite the first side when the patient interface device is positioned on the head of the patient, the second portion including a second rotation-resistant coupling positioned along the second portion so as to be disposed adjacent another ear of the patient when the patient interface device is disposed on the head of the patient;

a coupling member coupled to the frame member and structured to be coupled to the hose in order to communicate the flow of breathing gas from the gas flow generator to the frame member, the coupling member being fluidly coupled to and disposed opposite and distal the cushion; and a headgear assembly comprising:

a first arm member and a second arm member, each arm member comprising a first end and a second end disposed opposite the first end, the first end of the first arm member having a structure selectively engaged with the first rotation-resistant coupling in a manner which prohibits rotation of the first arm member with respect to the frame member in a first plane in which the first arm member is disposed, and the first end of the second arm member having a structure selectively engaged with the second rotation-resistant coupling in a manner which prohibits rotation of the second arm member with respect to the frame member in a second plane in which the second arm member is disposed; and a strap member coupled to the first arm member and the second arm member, and extending between each of the second end of the first arm member and the second end of the second arm member, wherein the first arm member comprises a body portion sized and configured to extend behind the ear of the patient when the patient interface device is disposed on the head of the patient, and wherein the second arm member comprises a body portion sized and configured to extend behind the other ear of the patient when the patient interface device is disposed on the head of the patient.

9. The patient interface device of claim 8, wherein each of the first rotation-resistant coupling and the second rotation-resistant coupling is an elongated slot; and wherein the structure of the first end of each arm member comprises a hook-shaped portion.

10. The patient interface device of claim 8, wherein the strap member is adjustably coupled to at least one of the first arm member and the second arm member.

11. The patient interface device of claim 8, wherein the body portion of each of the first arm member and the second arm member extends in a curved manner between the first end and the second end.

* * * * *